United States Patent
Chen

(10) Patent No.: US 9,534,999 B2
(45) Date of Patent: Jan. 3, 2017

(54) NANOSTRUCTURED BIOMIMETIC DEVICE FOR DETECTING A CANCER CELL OR CANCER CELLS

(71) Applicant: Ellen T. Chen, Germantown, MD (US)

(72) Inventor: Ellen T. Chen, Germantown, MD (US)

(*) Notice: Subject to any disclaimer, the term of this patent is extended or adjusted under 35 U.S.C. 154(b) by 517 days.

(21) Appl. No.: 13/919,216

(22) Filed: Jun. 17, 2013

(65) Prior Publication Data
US 2014/0178925 A1  Jun. 26, 2014

Related U.S. Application Data

(60) Provisional application No. 61/660,072, filed on Jun. 15, 2012, provisional application No. 61/660,080, filed on Jun. 15, 2012, provisional application No. 61/660,690, filed on Jun. 16, 2012, provisional application No. 61/691,632, filed on Aug. 21, 2012.

(51) Int. Cl.
*G01N 27/327* (2006.01)
*G01N 15/10* (2006.01)
*B82Y 30/00* (2011.01)
*A61B 5/00* (2006.01)

(52) U.S. Cl.
CPC ...... *G01N 15/1031* (2013.01); *G01N 27/3278* (2013.01); *A61B 5/0091* (2013.01); *B82Y 30/00* (2013.01); *G01N 2015/1006* (2013.01); *G01N 2610/00* (2013.01); *G01N 2800/7028* (2013.01)

(58) Field of Classification Search
CPC .............. G01N 27/3278; G01N 27/327; G01N 27/3272; G01N 2610/00; G01N 2800/00; G01N 2800/7028
See application file for complete search history.

(56) References Cited

U.S. PATENT DOCUMENTS

| | | | |
|---|---|---|---|
| 6,582,583 B1* | 6/2003 | Chen | B82Y 15/00 |
| | | | 204/403.01 |
| 2008/0237063 A1* | 10/2008 | Chen | C12Q 1/006 |
| | | | 205/777.5 |

OTHER PUBLICATIONS

Zhao "Highly sensitive identification of cancer cells by combining the new tetrathiafulvalene derivative with a β-cyclodextrin/multi-walled carbon nanotubes GCE," Analyst, 2010, 135, 2965-2969.*

* cited by examiner

*Primary Examiner* — Alexander Noguerola

(57) ABSTRACT

The present invention provides a single cancer direct detection device comprises an electrode having a nanopore biomimetic membrane inducing a bio-communication signal by cancer cells selectively under antibody-free and label-free condition. Methods of detecting cancer cells and monitoring cancer progresses in a contour map format are also discussed. In particular, the cancer cell heat release map comprises multiple variables correlations, a ratio of "Action potential/Resting potential" (RAPRP) as a special biomarker for the variable along with other variables of current or concentration makes visual display cancer progresses possible compared with normal cells which have negligible heat release.

16 Claims, 20 Drawing Sheets

Fig 1
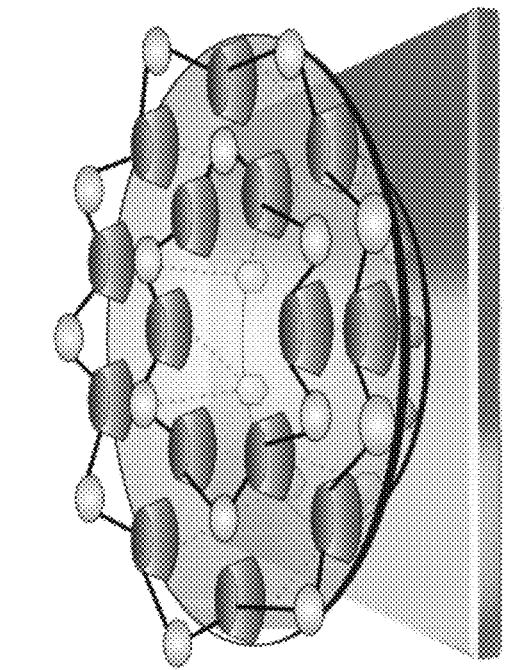
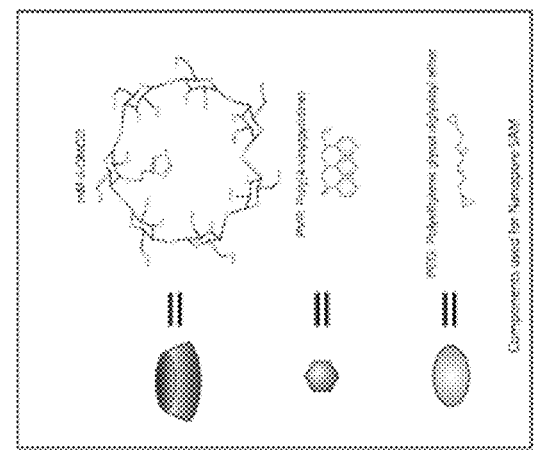

Fig 2
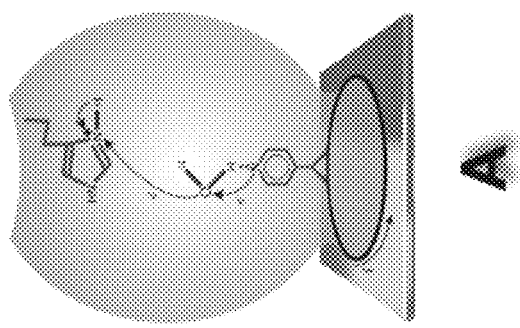
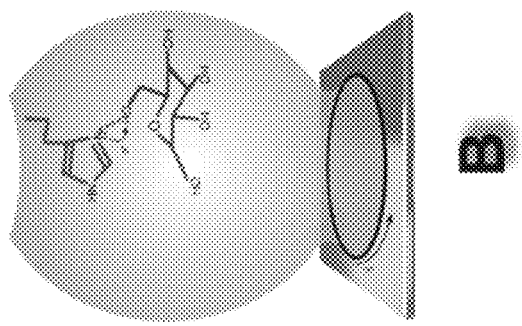
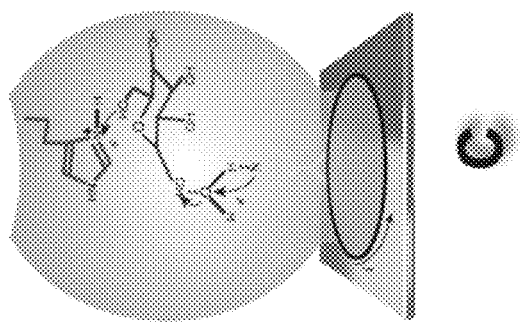

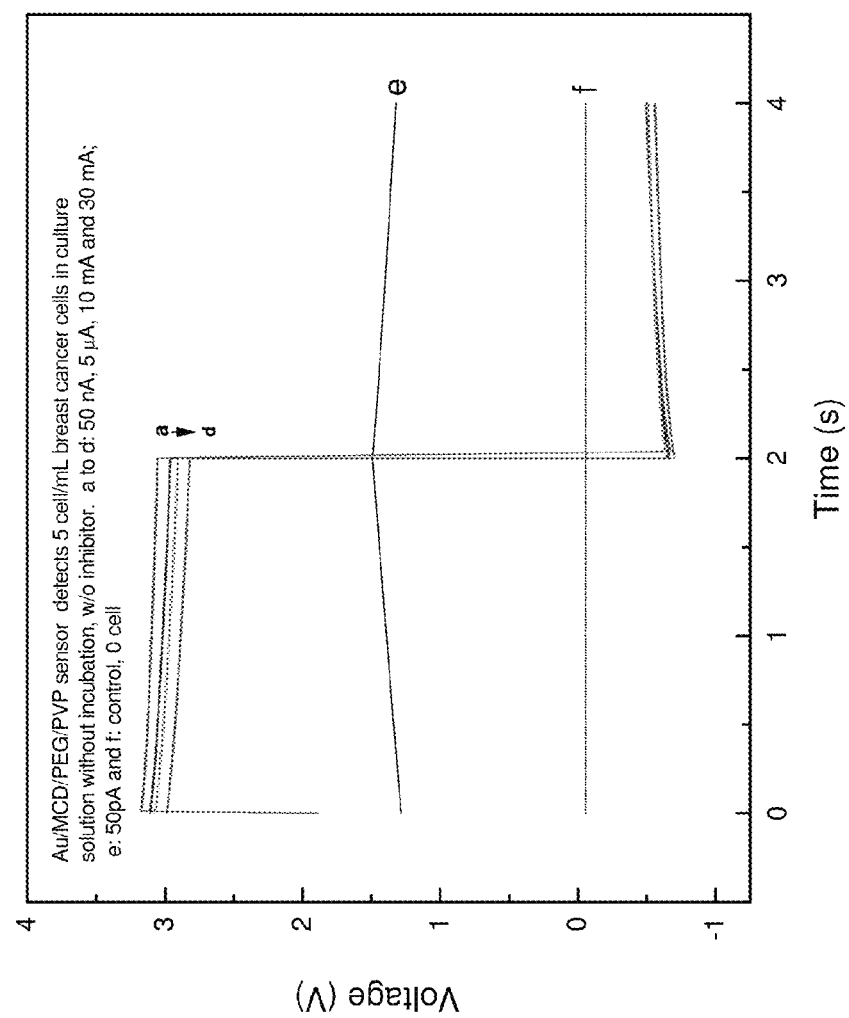

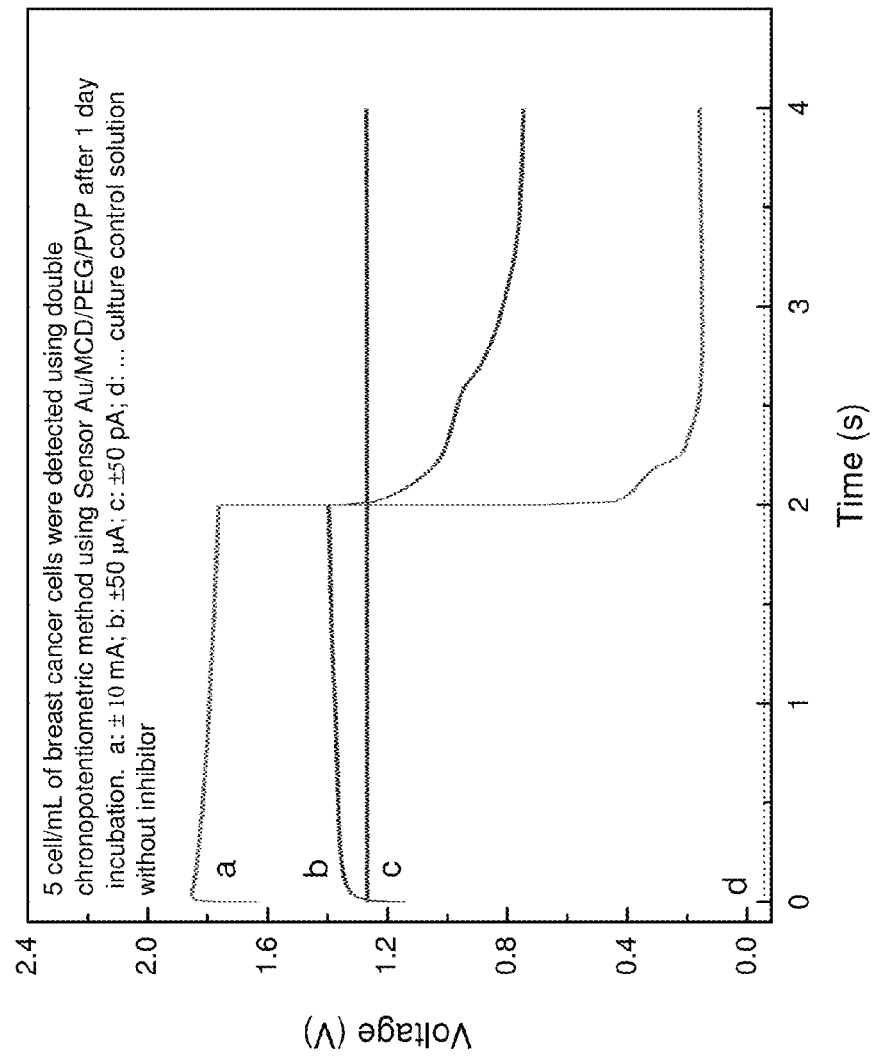

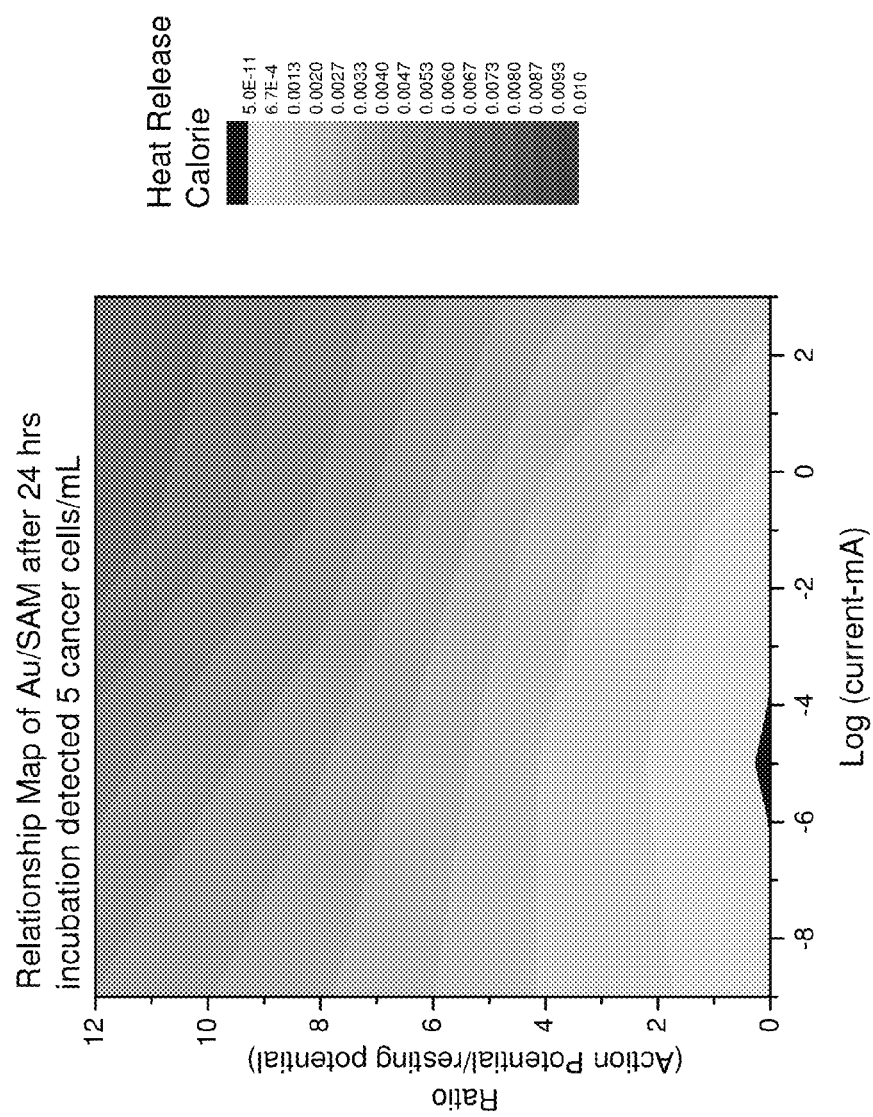

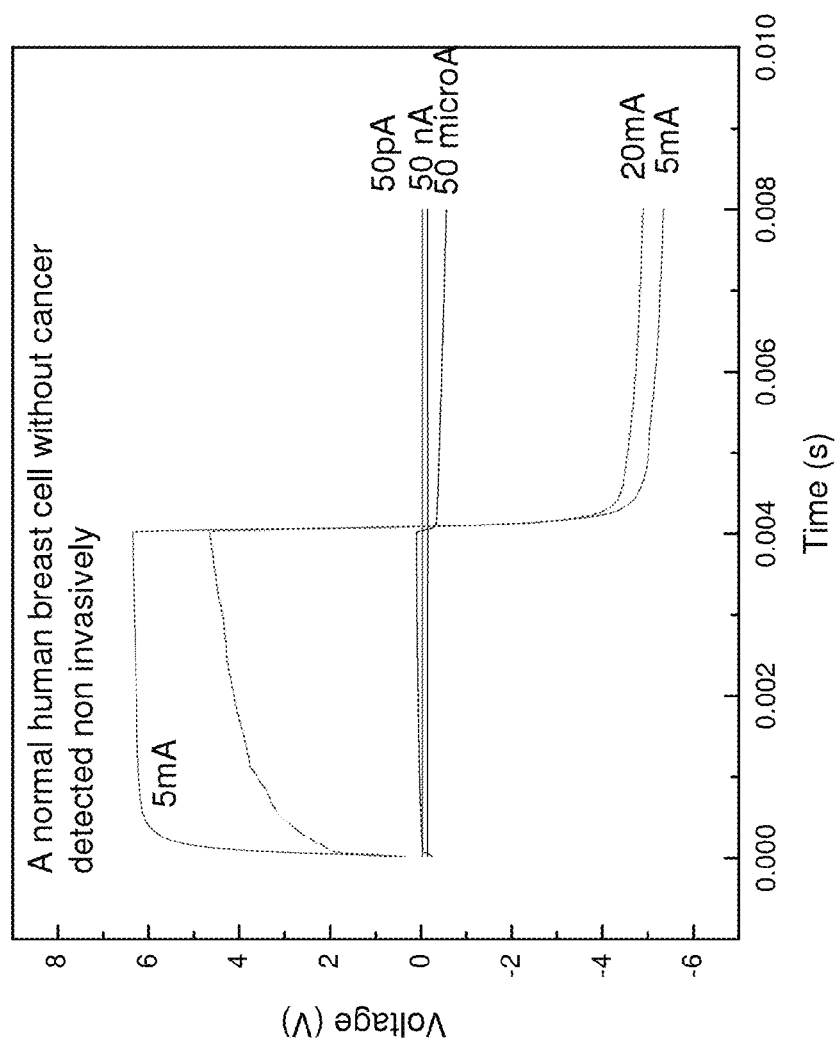

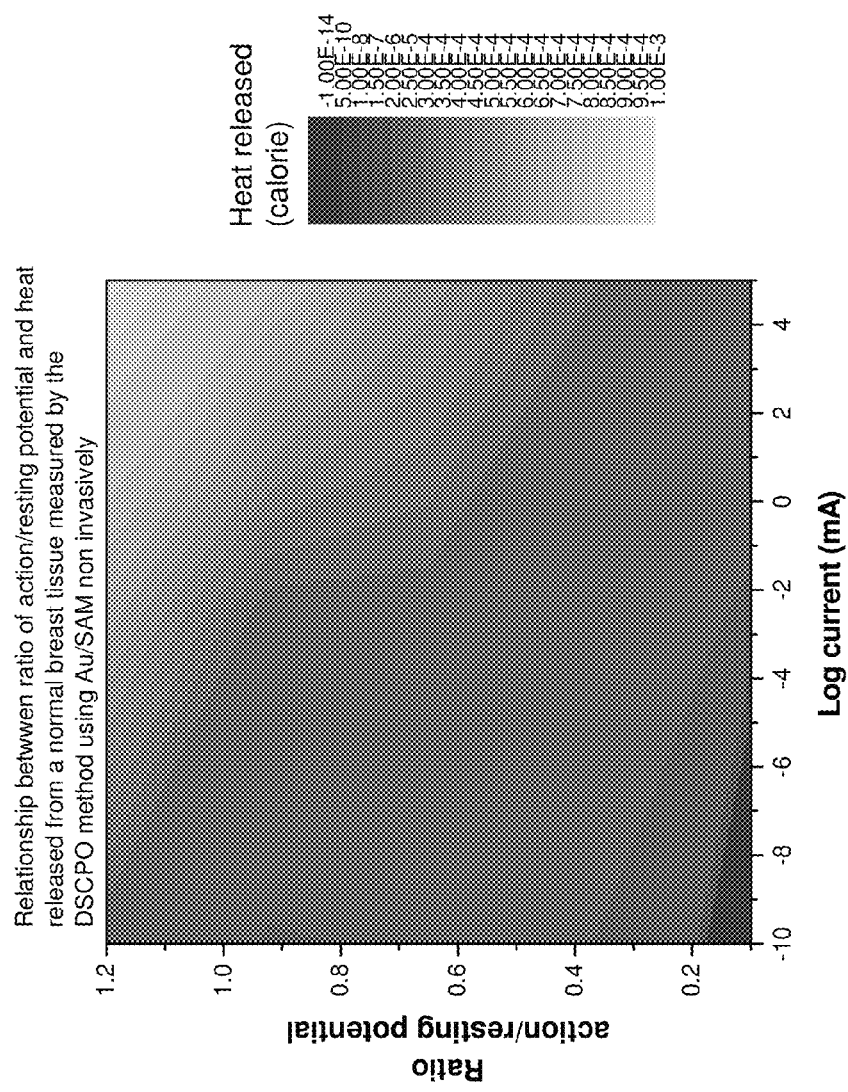

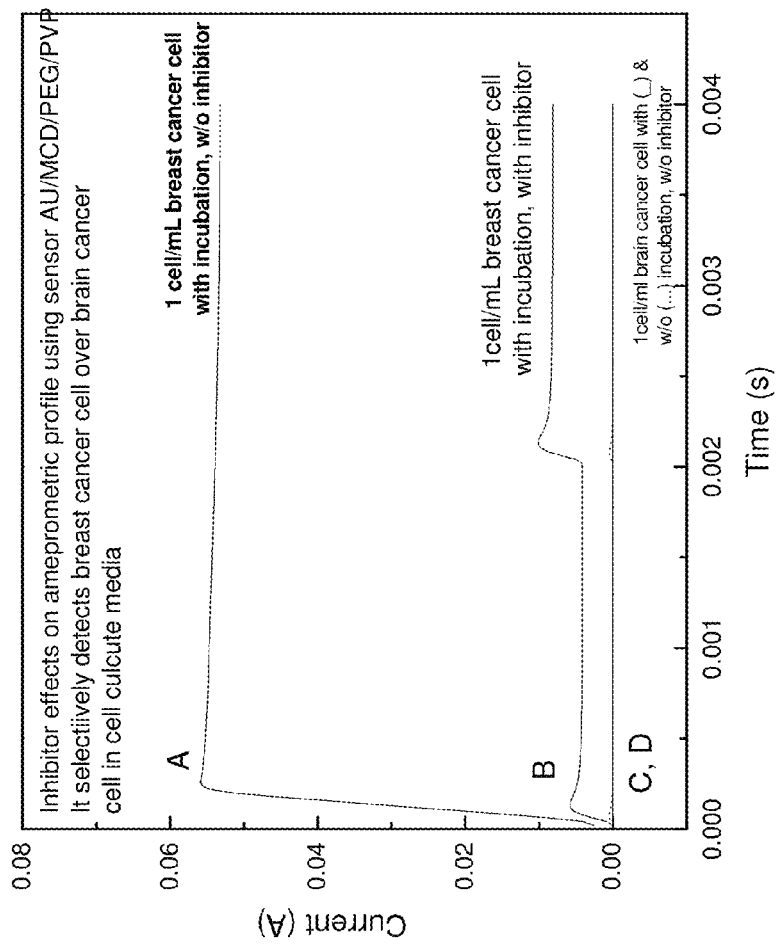

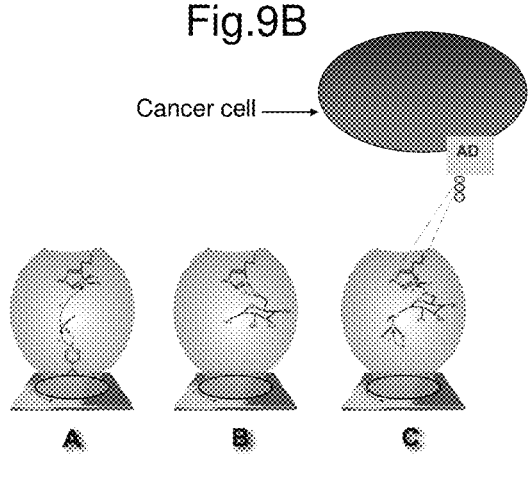
Fig.9B

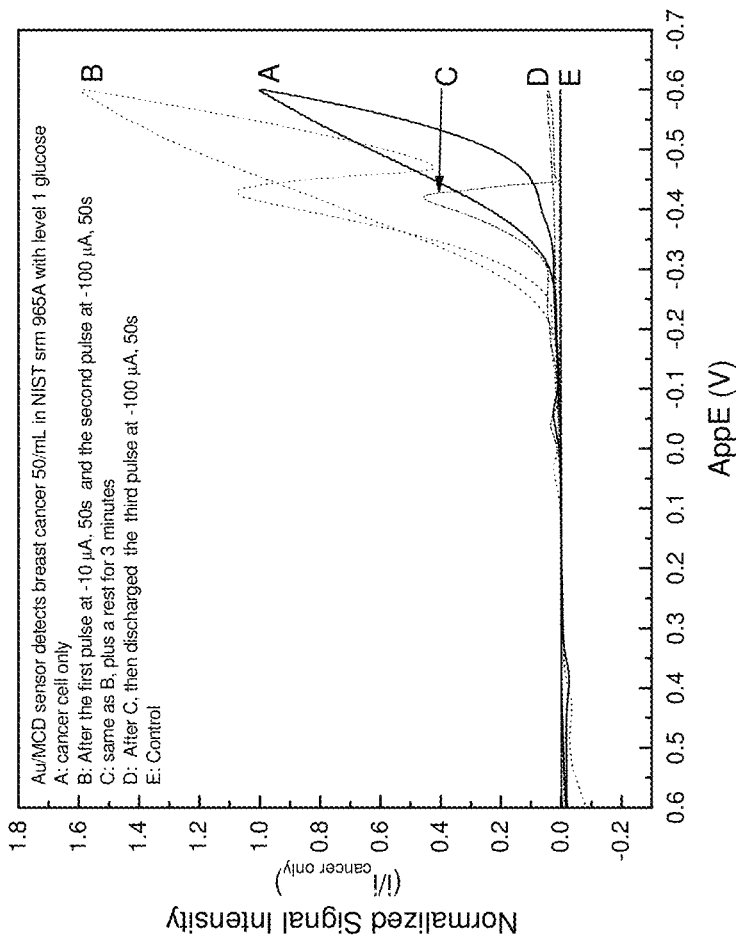

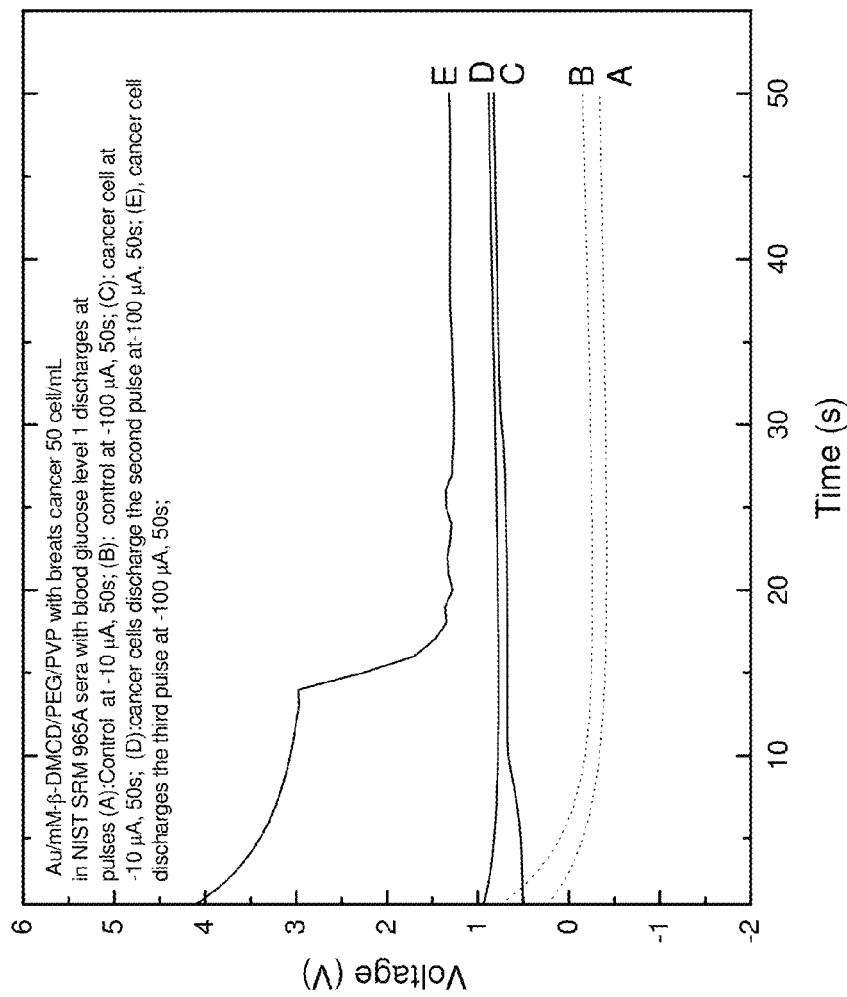

NANOSTRUCTURED BIOMIMETIC DEVICE FOR DETECTING A CANCER CELL OR CANCER CELLS

CROSS REFERENCE TO RELATED APPLICATIONS

This application is a nonprovisional application of U.S. provisional application No. 61/660,072, filed 15 Jun. 2012 and entitled "Nanopore Structured Biomimetic Sensor Device;" is a nonprovisional of U.S. provisional application No. 61/660,080, filed 15 Jun. 2012 and entitled "Nanopore Structured Biomimetic Sensor Device;" is a nonprovisional of U.S. provisional application No. 61/660,690, filed 16 Jun. 2012 and entitled "Nanopore Biomimetic Device;" and is a nonprovisional of U.S. provisional application No. 61/691,632, filed 21 Aug. 2012 and entitled "Nanopore Structured Biomimetic Device." The disclosure of each aforementioned application is incorporated herein by reference in its entirety.

FIELD OF THE INVENTION

The present invention relates to the field of cancer progress monitoring devices and, in particular, to devices handheld comprising a Nanostructured Biomimetic membrane, through functions of spontaneously discharging electric pulses and charging electric pulses at real time, hence the heat released by cancer cells can be 3 dimensionally mapped in the contour form and the degree of the cancer prognosis severity can be monitored.

BACKGROUND OF THE INVENTION

It is a well recognized phenomenon that cancer cells have abnormal cell membrane potential [1-3]. The conventional biopotential method used for diagnosing cancer is lacking in sensitivity and selectivity [3]. Biologists measure cell membrane action and resting potentials with burdensome instrumentation with time consuming procedures. A recent report shows breast cancer cell division caused a membrane potential increase [4] due to variations in ion channel expression. However, the method requires a time consuming large computer algorithm for modeling, and still lacks selectivity and sensitivity. A recent paper reported that the measured neural cell membrane spiking potential has a signal to noise ratio of 2 [5]. Because the normal cell membrane action potential is 58 mV, and −70 mV is for the resting potential [6], the small signals are very easily buried in the background noises [7] that can cause problems to pediatric neurologist and intensive care unit doctors who need strong signals to monitor and diagnose the neonatal neurological diseases [7]. There is very few, if any, to build a device that can induce receptors of cancer cells spontaneous and direct interact with the artificial receptor of the membrane of the device without using antibody or labeling. The amplified signals are several orders of magnitude higher in signal to noise ratio than the conventional methods, will provide means to enhance the sensitivity and selectivity of the detection. The goal of this invention is to develop such a handhold device by fabricating a nanopore structured biomimetic membrane on a gold chip with an imidazolium receptor in the polymer network to induce the direct biocommunication to cancer surface receptors without using antibody, and without labeling in order to overcome the current technology drawbacks and through the functions of discharge and change electric pulses at real time, hence the transformed energy from the cancer cells can be mapped out in three dimension with a contour form, therefore the progress of the cancer can be monitored visually, that will be beneficial to patients and medical doctors.

SUMMARY OF THE INVENTION

The present invention provides a novel electrochemical device and a cancer cell heat release map method to visually display the cancer progresses. The novel device comprises an electrode having a nanopore biomimetic electron-relay network with imidazolium-ATP of cancer cell-water-pyridine at the active sites that mimic the electron-relaying between His 516 and N(5)-FAD of GOx for the purpose to selectively detect triple-negative breast cancer cell at single cell concentration and it rejects brain cancer cell. The device is fast in millisecond to detect cancers without sample preparation and without interference from other substances, such glucose and proteins under reagent-free conditions. A unique biomarker of the ratio of "Action/Resting" cell membrane potential can be used to monitor the cancer progress against the normal cells. A visual contour map of a multiple variable correlation method provided to assess the heat release from the cancer cells against the normal cells is presented. The device for a potential therapeutic application was demonstrated by discharge voltage pulses from the live cancer cells with release extra energy that the cells possessed until it returns to a normal status in terms of normal cell membrane action/resting potential ratio.

It is an object of the present invention to provide a new generation of cancer detection device has selectivity among single cancer cell between brain cancer and breast cancers through a nanostructured biomimetic membrane sensing device under antibody-free an labeling-free conditions. It is an object of the present invention to provide above described device system with another function of visualizing 2D contour heat release map from the cancer cells based on a multiple variable energy conversion method.

It is another object of the present invention to establish a ratio of cell membrane action potential vs. resting potential as the land marker ratio of "action potential" vs. "resting potential" (RAPRP) values that distinguish between the normal cells and the cancer cells, as the biomarker, under antibody-free and labeling-free conditions. It is a further object of the present invention to provide a device having therapeutic function of healing of breast cancers by inducing the cancer cells to release extra energy that it possessed through spontaneously discharge electric pulses, while real time monitoring the ratio of action/resting membrane potential/heat release map.

BRIEF DESCRIPTION OF THE DRAWINGS

FIG. 1 Illustrates an art work for the model used to construct the Au-nanopored His 516 receptor-CD SAM electrode. The moiety of the receptor-CD was cross-linked with PEG and PVP and a nanopore structured SAM was self-assembled.

FIG. 2 (A) illustrates the initial step of forming the electron-relaying system in an imidazolium-water-pyridine before glucose entered the nanopore. (B) illustrates the second step of "host-guest" inclusion between imidazole and glucose when glucose solution was added in the buffer. (C) illustrates the third step of electron-relay system. It has rearranged to form an imidazolium-glucose-water-pyridine electron-relaying system at the active sites that mimic the electron-relaying between His 516 and N(5)-FAD of $GO_x$ through the hydrogen bonding.

FIG. 5A illustrates the effect of current on DSCPO profiles without incubation and without inhibitor under 5 cancer cells/mL concentration with current change from a to d: 50 nA, 50 µA, 10 mA, 30 mA; e: 50 pA, f: control without cell;

FIG. 6A Illustrates the effect of current change on DSCPO profiles with 1 day incubation and without inhibitor under 5 cancer cells/mL concentration with current change from 10 mA (a), 50 µA (b), 50 pA (c) and without cancer cell (d).

FIG. 6B illustrates the 5 breast cancer cells heat released with 24 hrs incubation.

FIG. 7A illustrates current change effects on the DSCPO profiles of a normal living breast cell in a non invasive manner from a to e: 50 pA (a), 50 nA (b), 50 µA (c), 30 mA (d) and 20 mA (e), respectively.

FIG. 7B illustrates the normal breast cell heat release map.

FIG. 8 illustrates the ameprometric profiles using the AU/MCD sensor. (A) breast cancer cell (1 cell/mL) with incubation without inhibitor; (B) Breast cancer cell (1 cell/mL) with incubation and with an inhibitor; (C) Brain cancer cell (1 cell/mL) with incubation without inhibitor; (D) Brain cancer cell (1 cell/mL) without incubation and without inhibitor in cell culture media.

FIG. 9B depicts the cancer cell's bio-communication in an electron-relay between the ATP of the cancer cell and the imidazolium, water, pyridine groups at the active sites that mimics the electron-relay network between His 516 and N(5)-FAD of $GO_x$ in the presence of glucose.

FIG. 10 illustrates CV profiles of pulse effects on live breast cancer cell signal with Au/MCD sensor at 50 cell/mL in NIST standard human serum SRM 965A with certified level 1 glucose at room temperature: A: cancer cell only; B: After the first pulse at −10 µA, 50 s and the second pulse at −100 µA, 50 s; C: same as B, plus a rest for 3 minutes; D: After C, then discharged the third pulse at −100 µA, 50 s; E: Control.

FIG. 11 illustrates Au/MCD/PEG/PVP sensor with breast cancer 50 cell/mL in NIST standard human serum SRM 965A with blood glucose level 1 discharges at pulses (A): Control at −10 mA, 50 s; (B): control at −100 mA, 50 s; (C): cancer cell at −10 mA, 50 s; (D): cancer cells discharge the second pulse at −100 mA, 50 s; (E), cancer cell discharges the third pulse at −100 mA, 50 s at room temperature.

DETAILED DESCRIPTION OF THE INVENTION

Example 1

Fabrication of the Nanostructured Biomimetic Self-Assembling Membranes (SAM)

Reagent grade poly (4-vinylpyridine) (PVP), polyethylene glycol diglycidyl ether (PEG), were purchased from Aldrich-Sigma. The PVP was recrystallized in methanol. The mono imidazol derivative dimethyl β-cyclodextrin (mM-β-DMCD) was generally synthesized according to the published procedures [8]. The gold chips were purchased (Fisher Scientific) and the mixture solutions with proper compositions and procedures were followed by published literature in [9].

Example 2

Characterization of the Membrane of AU/SAM

The morphology of the AU/SAM was characterized using a Dimension 3100 Atomic Force Microscope (AFM) (Bruker Nano, CA). FIG. 1 is an art illustration of the model used to construct the Au-nanopored sensor cross linked with polymers and modified cyclodextrins by SAM method. FIG. 1 illustrates an art work for the model used to construct the Au-nanopored His 516 receptor-CD SAM electrode. The moiety of the receptor-CD was cross linked with polyethylene glycol diglycidyl ether (PEG) and poly(4-vinylpyridine) (PVP) and self-assembled a nanopore structured SAM through hydrogen bonding. Possible driving forces to form such a nanopore could be the changes in the heat of formation in the active site and the change of free energies of solvation that are favorable to the electron-relay processing. The $pK_a$ value difference between the receptor His 516 and the pyridine, and the difference of hydrophobicity between the internal cavity of CD and the pyridine of PVP may also play an important role in the self-forming nanopore as shown in FIG. 2. FIG. 2 illustrates the proposed electron-relaying model in the active sites with and without glucose entered the nanopore. FIG. 2(A) illustrates the initial step of forming the electron-relaying system of the imidazolium-water-nitrogen relay before glucose entering the nanopore. Observations of the DET current confirmed the electron transfer step using a cyclic voltammetric scan method. FIG. 2(B) illustrates the second step of "host-guest" inclusion between imidazole and glucose when adding glucose solution in the pH 7 buffer. This step temporally disturbed the electron-relay flow, that indicates the analyte glucose entered the nanopore and had an influence on the DET current flow. FIG. 2(C) illustrates the third step of electron-relay system that has rearranged to form an imidazoliumglucose-water-pyridine electron-relaying at the active sites that mimic electron-relaying between His 516 and N(5)-flavin adenine dinucleotide (FAD) of $GO_x$.

Figure 3A:
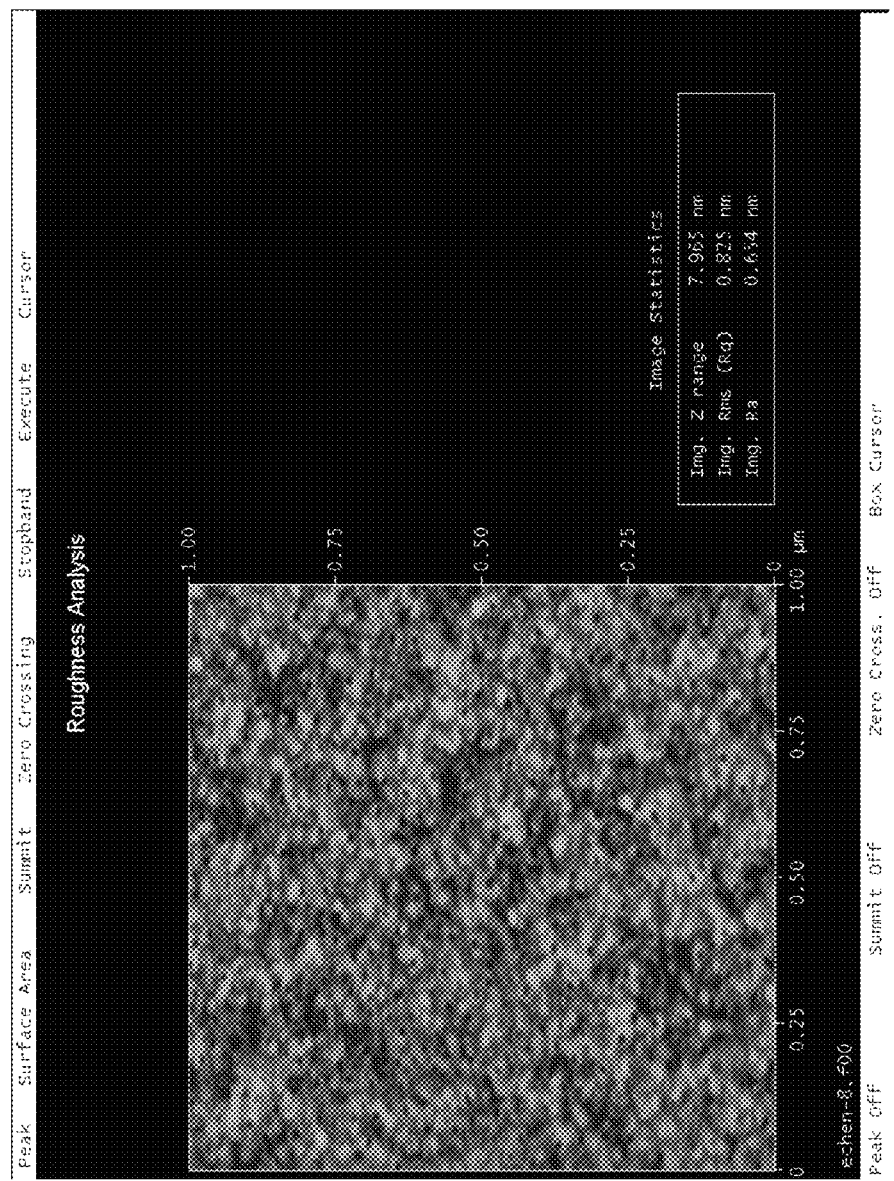
FIG. 3A shows two-dimentional atomic force microscopy (AFM) image of nanopore structured mM-β-DMCD/PEG/PVP, here mM-β-DMCD's short name as MCD, SAM with an internal receptor imidazolyle. Brighter areas represent higher topography. The roughness measurements Peak-to-Valley (Z range), Root Mean Square (RMS), and Average Roughness ($R_a$) are also shown for this image.
Figure 3B:
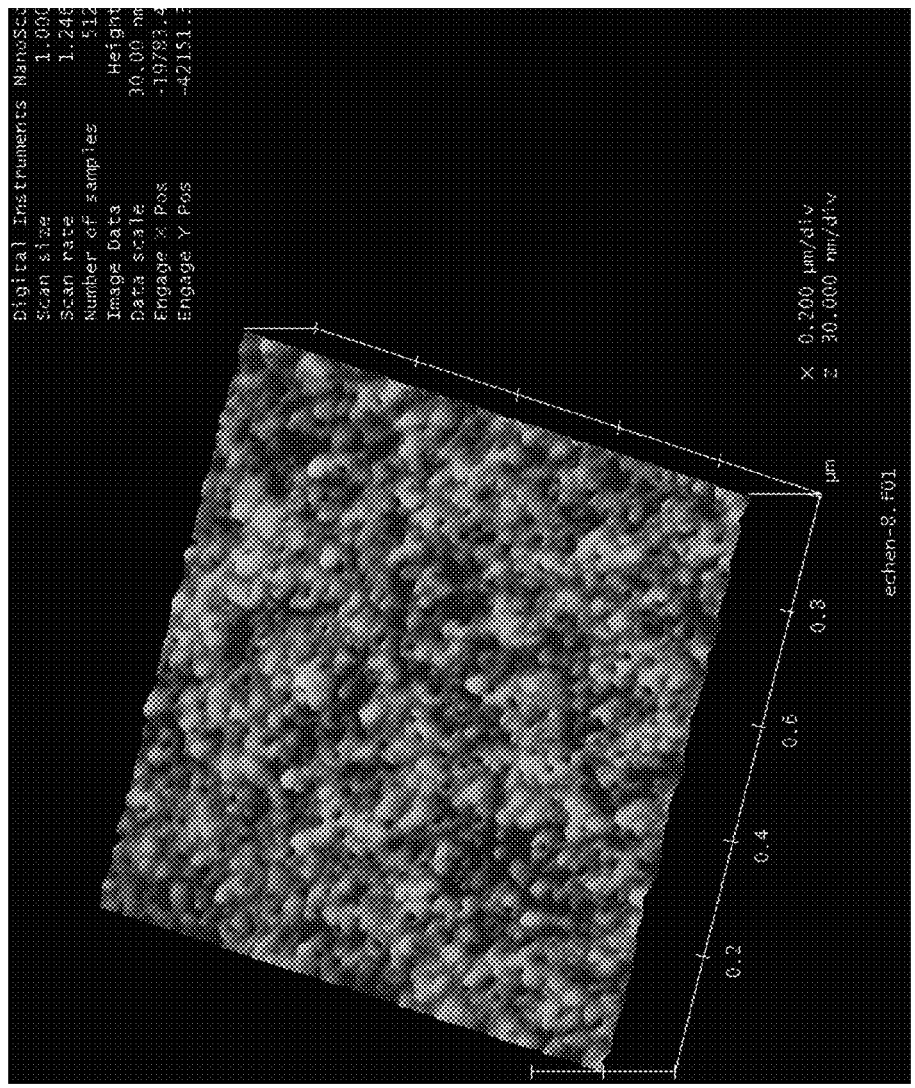
FIG. 3B shows 3D AFM image for the same sensor as in FIG. 3A.
Figure 3C:
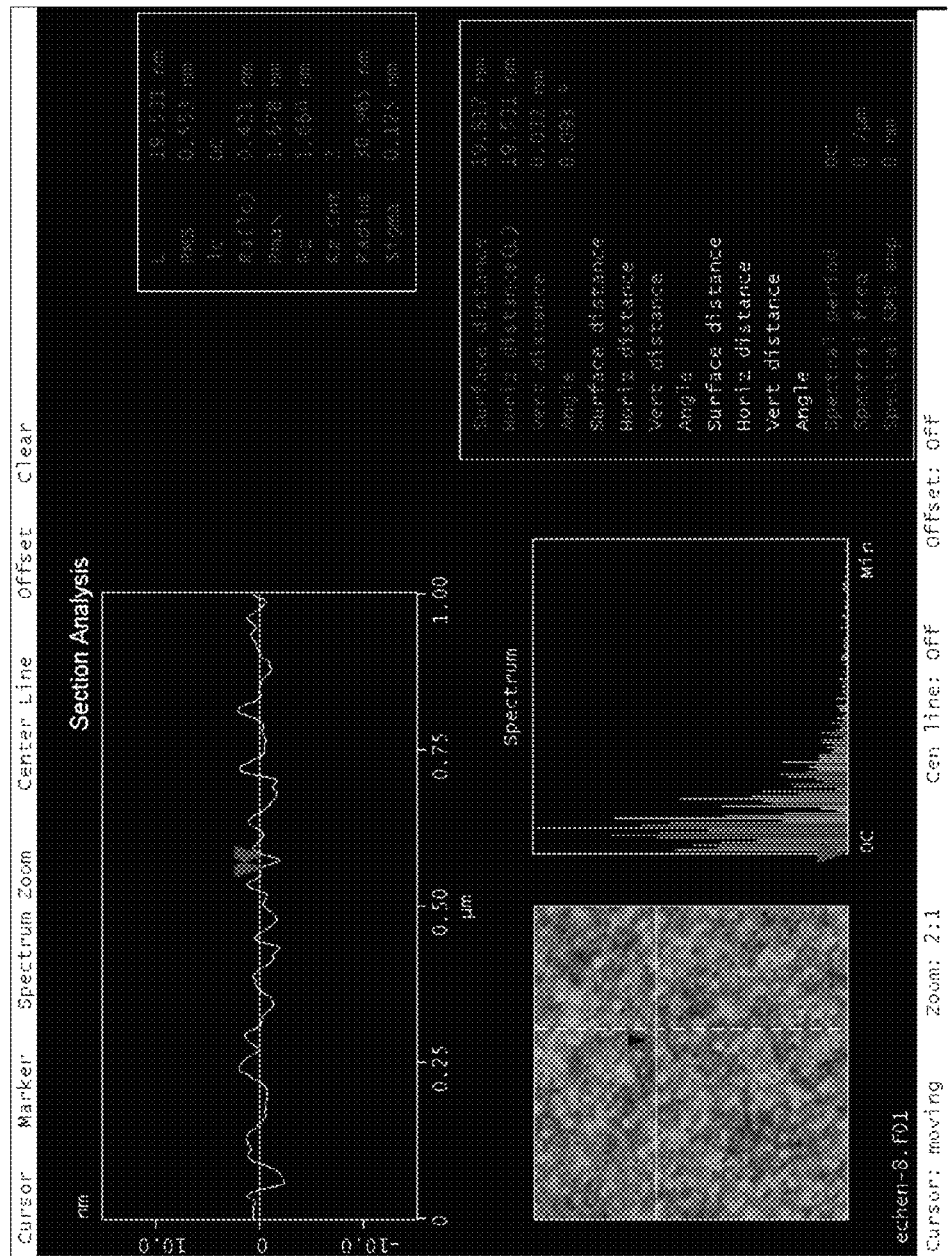
FIG. 3C shows the cross-section analysis of nanopore size measurement of the same sensor as in FIG. 3A.

The surface structure, shown in FIG. 3A, was scanned by TappingMode AFM using a silicon cantilever and a tip with a 5-10 nm radius and resonance frequency of 300 kHz [10]. The roughness of the SAM was 0.82 nm Root-Mean-Square (RMS) as shown in FIGS. 3A and 3B. FIG. 3C is a cross-section analysis with pore size measurement as 19.5 nm in average.

Example 3

Human Cancer Cell Line MDA-MB-231 and the Glioblastoma Brain Cancer Line SNB-19

Figure 4A:
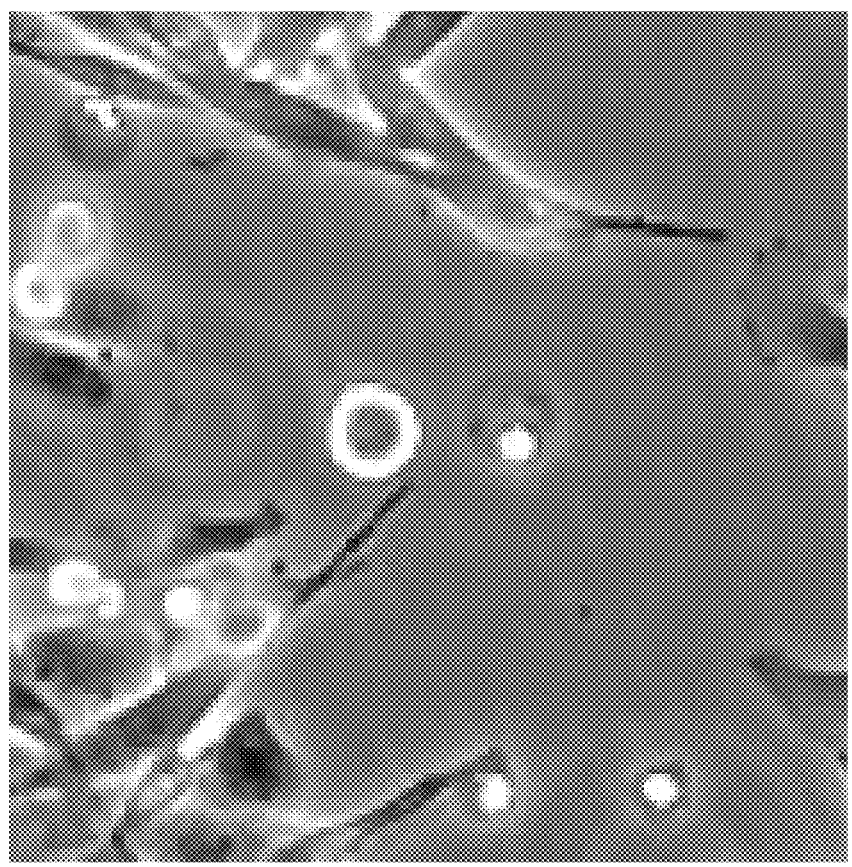
FIG. 4A shows an image of the human breast cancer cells of MDA-MB-231 in a growing medium of DMEM.
Figure 4B:
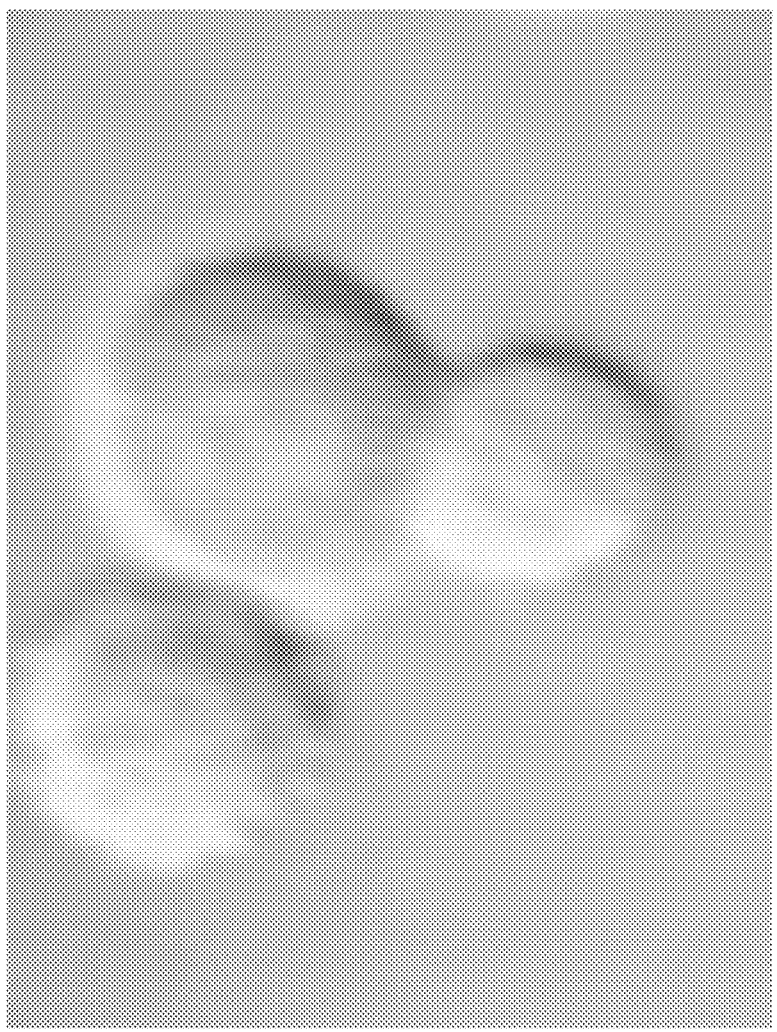
FIG. 4B shows an image of the human brain cancer cells of Glioblastoma brain cancer line SNB-19 in a growing medium of DMEM.

Breast cancer cell samples are human adenocarcinoma cells line MDA-MB-231 as shown in FIG. 4A taken from breast cancer tissue. The glioblastoma brain cancer cells samples are human neuro blastoma line SNB-19 as shown in FIG. 4B. The cell cultures are held in a base growing medium of DMEM (Dulbecco/Vogt Modified Eagle's minimal essential Medium—a common growth culture medium used for human cell incubation) (Invitrogen, CA infused with a 10% concentration of FBS (fetal bovine serum), 10 mM HEPES, 100 units/mL penicillin/Streptomycin and 2 mM L-glutamine. It was kept in a normal atmosphere at a temperature of 37.0° C. with 10% $CO_2$ and humidified air. The cancer cells in the DMEM media were incubated for 24 hrs. Before test the cancer cells, dilution procedures were conducted.

Example 4

The Single Cancer Cell Selectivity

The selectivity of the sensor device towards detecting the breast cancer cells compared with that of normal living breast cells were conducted at room temperature by the Double Step Chronopotentiometry (DSCPO) method. The normal breast specimen was tested by the DSCPO method in a non-invasive manner, that the wetted sensor was directly attached on the skin of the breast of the subject, whom was consent and was approved with the IRB.

The DSCPO method was used for evaluation of the sensor performance for cancer detection under fixed current conditions. Changes of current effects on the "action potential" and "resting potential" were conducted in the range from pA to mA in vitro culture medium at room temperature. All experiments were finished within 1 hr. Changes of cell concentrations effect on the potentials were conducted in the ranges from 1, 5, 100, to 200 cell/mL using an electrochemical work station (Epsilon, BASi, IN). The 16 channel AU/SAM electrode chip configuration was mentioned in *Section of Fabrication of the Nanostructure Self-Assembling Membrane (SAM) Gold Sensor Chip*. The center circular electrode is the working electrode, and the adjacent gold electrodes are the auxiliary and the reference electrode, respectively.

Selectivity was further confirmed by an amperometric method using the MCD sensor as shown in FIG. 8. It demonstrates this sensor selectively detecting breast cancer cell over brain cancer cell at 1 cell/mL concentration. FIG. 8 illustrates the amperometric profiles. (A) refers to the breast cancer cell with incubation without inhibitor; (B) refers to breast cancer cell with incubation with an inhibitor; (C) refers to the brain cancer cell with incubation without inhibitor; (D) refers to the brain cancer cell without incubation without inhibitor. It was observed that the inhibitor reduced the breast cancer signal strength by 92%.

The selectivity study was also conducted at room temperature by a Cyclic Voltammetric method. (CV) to detect the breast cancer cells and the brain cancer cells. The scan rate was constant at 20 mV/s for the CV method. It was shown in FIG. 9A, that the MCD sensor only selectively detects breast cancer cell with peaks signal intensities of ±0.025 A at 0.0 mV for the solid red curve over brain cancer cell without peak observed of (the black dotted line) at 1 cell/mL concentration against control in blue solid line.

Example 5

Effect of Current Change with or Without Cell Incubation

FIGS. 5A and 6A illustrate current change effect on the DSCPO profiles under 5 breast cancer cell/mL concentration with or without 1 day incubation, respectively, against the controls that did not have cancer cell as shown in FIG. 7A. Both figures were without inhibitors. It is obvious that with 1 day incubation, the DSCPO's action and resting potential profiles moved up to all positive potential fields, especially for resting potential, indicating the cancer cells are not in a normal "resting potential" stage, i.e, about −70 mV, have critically impacted the ratio of action/resting potential (RAPRP), hence the results of RAPRP are larger than that of without incubation. The action potential signals were increased as current increased drastically than that of without incubation. For without incubation, there were superimposed curves for resting potentials regardless the current changes. Current changes had smaller impact on the potentials for without incubation than that of with 24 hrs incubation.

Example 6

Effect of Current Change on a Normal Breast Cell

Current change effect on a living normal breast cell was illustrated in FIG. 7A. The amplitude of curves at the action and resting potential fields are symmetric alone the zero line, indicating the RAPRP values are close to 0.75-0.9 range, which is at a normal electrophysiological situation [6]. The sensor is attachable on to the live human breast skin non-invasively. This sensor demonstrated its capability to selectively induce a bio communication more favorably to cancer cell rather than to a normal cell at very sensitive concentration level, because cancer cells with high negative charge density tend to direct hydrogen bonding to the positive imidazolium receptor in the sensor membrane.

Example 7

The Ratio of "Action Potential/Resting Potential" of Cell Membrane as a Biomarker The discharge potential was defined as "action potential", and the charge potential defined as "resting potential. The duration time is 2 s for action or resting potential for the model cancer sensor study. The absolute value of action potential divided by the resting potential was defined as the ratio of action potential vs. resting potential. The ratio was used for assess of cell heat release by a Contour Map Multiple Variable Correlation method (CMMVC).

Example 8

Assessing Cell Heat Release

The CMMVC method was used for assess of cancer cell heat release. Two variables chosen for assessing the heat released by cancer cells (as Z axis) were 1. Ratio of "Action potential" vs. "Resting potential" (as Y axis) and 2. Cell concentration as X axis was used for cell concentration factor study. Similarly, it was only a change in X axis to current, while other factors are remain the same, was conducted for the current factor study. The results of absolute difference between action and resting potential at a given cell concentration under a known current, were used to multiply the current and then multiply the time duration of the potential fired by the equation of $J=I \cdot \Delta V \cdot t$, I is current in ampere, $\Delta V$ is voltage difference in volt and t is time in second. J is Joule. Joule divided by a 4.184 conversion factor gives the calorie released.

Example 9

Breast Cancer Cell Heat Release Visual Map

Figure 5B:
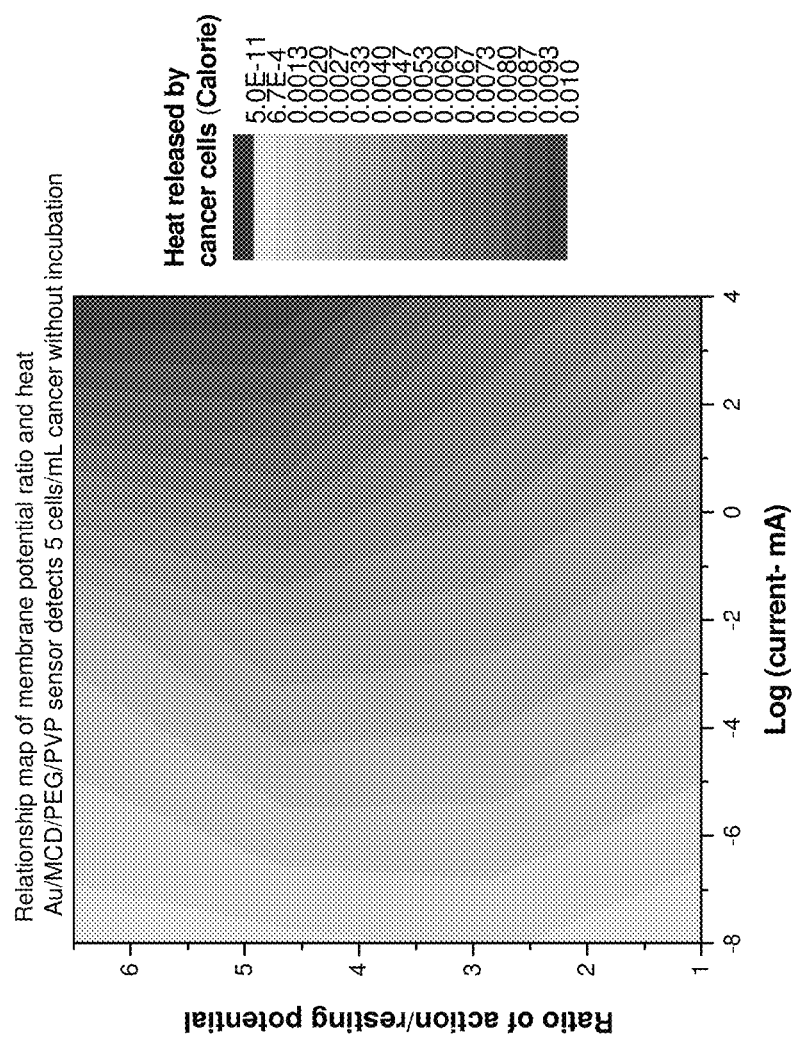
FIG. 5B illustrates the 5 breast cancer cells heat released without incubation.

The results shown in red hot color in FIGS. 5B and 6B are for the CMMVC visual map for with or without incubation under 5 cancer cell/mL and ±10 mA current conditions. The gradient of red color change was positively correlated with the high abnormal RAPRP as discharge current rose to mA level for cancer cells and reflected in the visual map. The x axis is log current; the y axis is the ratio value and the z axis is the calorie. After a converting step, the blue color CMMVC map in FIG. 7B illustrates the normal breast cell heat release to the body, which is negligible. The order of magnitude higher in the RAPRP ratio associated with more heat release is the land marker behavior of the breast cancer cells under higher current is demonstrated. In contrast, the normal breast has the RAMP ratio close to the normal ratio range of 0.75-0.9 with no extra heat was released to the body regardless the current change over 50 pA to 20 mA range.

Example 10

A Bioelectronic Switcher at the Origin

Figure 9A:
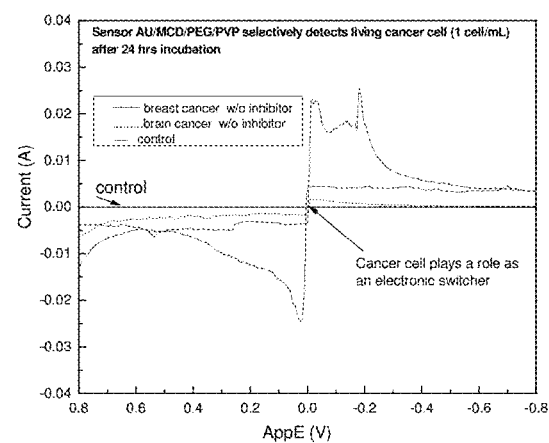
FIG. 9A illustrates the breast cancer detection device selectively detecting live single breast cancer cell (1 cell/mL) over live brain cancer cell (1 cell/mL) after 24 hrs incubation against control without cancer cell.

No one expects a single breast cancer cells can behave like an idea electronic semiconductor switcher and it switches current in opposite flow direction with the switch point at origin as shown in FIG. 9A. The switch "On" and "Off" are at the two cross-points [point 1 (−0.0047V, 0.0041 A), point 2 (0.005V, −0.0035 A) that passes origin (0,0)] about 0.45 ms and 0.8 ms, respectively, are observed. It was the sensor membrane's nanopore structure and the electron-relay function attracted the single breast cancer cell's attention as shown in the art model in FIG. 9B. The cancer cell has magnified the current at 46,074-fold compared with the control that was without cancer cell, indicating the energy of the cancer cell obtained may not only come from stealing the communication active receptor sites for glucose (we did not see the glucose peak, originally it was designed the sensor for detecting glucose [9]), but also from the "Idea Diode" like capability of the cancer cell, in order to maintain its high action membrane potential—a self-compensation of energy system exists, will put cancer cell in an advantage position (Driver seat) than the normal cell. The "Butterfly" characteristic semiconductor I-V curves with high current in ±25 mA when the switch is at "on" position and a very narrow switch window (±5 mV) and short switch time of when the switch is "Off" in less than 1 ms has proven the triple-negative breast cancer's uniqueness in its eternal cell structure, like a "biosemiconductor".

Example 10

Evaluation of the Potential Therapeutic Applications

The cancer cells possessed extraordinary high energy than that of normal cell led one to believe that a method to release the extra energy from the cancer cell would be the most effective way to heal cancer than use drugs and radiation. FIG. 10 illustrates CV profiles of pulse effects on signal of live breast cancer cell with the MCD sensor at 50 cell/mL in NIST standard human serum SRM 965A with certified level 1 glucose at room temperature. It was observed that after the first pulse at −10 µA, 50 s as shown in FIG. 11 (C), the peak current intensity at −0.53V suddenly increased by 60% and the appearance of second peak located at −0.33V toward a more positive potential field, along with the cross-points occurred at −0.44V and −0.36V as shown in FIG. 10 (B), that indicate cancer cells urgent to use the "biosemiconducor energy switch" approach to compensate its energy lose, and trying to maintain the membrane active potential as before, hence we observe two switch points along with the signature butterfly curves. There is no butterfly CV curve observed after the second pulse released as shown in FIG. 11 (D) and the peak intensity of the CV curve was reduced by 60% compared with the original peak intensity of cancer alone in FIG. 10 (C), indicates the cancer cell lost its footing and is no longer to maintain the high action potential, that became less aggressive compared with the original peak. After the third pulse as shown in FIG. 11 (E), the cancer peak was totally gone as shown in FIG. 10 (D) against control (E), indicates this method works and effective. The benefits of this method are its noninvasiveness pain-free and effective within 3-4 minutes, each pulse lasts 50 s that is minimum discomfort, and no side effect. The specific capacitance values are 4.14 mF/g, 40.94 mF/g and 8.20 mF/g at the first 15 s discharge at first, second and third pulses respectively.

The cancer cells enhanced the heterogonous electron transfer rate constant $k_s$ 1.54-fold (142/s) compared without the presence of cancer cells in a cell culture media, that the $k_s$ of the direct electron transfer rate constant is 92/s [11]. The triple-negative breast cancer cell is capable to form an electron-relay network with imidazolium-ATP of cancer cell-water-pyridine at the active sites that mimic the electron-relaying between His 516 and N(5)-FAD of $GO_x$ as shown in FIGS. 9A and 9B. There was no glucose peak in the curve indicates cancer cell sealed the position for itself even though originally the sensor was designed for glucose [9]. The uniqueness of the sensor here reported is the nanopore structure and the electron-relay network promoted the effective energy transfer between ATP and ADP within the cancer cell as seen the two larger peaks in FIG. 9A, even though the calculation of $ks=\alpha nFv_c/RT$, where $\alpha$ is the electron transfer coefficient, n is the number of electrons, F is the Faraday constant, $v_c$ is the scan rate, R is the gas constant, and T is temperature [12], is still based on irreversible situation because of the two cross-points exist between the two peaks. This may provide an evidence that the successful energy exchange has accomplished by the "idea semiconductor switchers" of the cancer cells and plus the eternal electron-relay and nanopore structure of the sensor membrane, made the cancer cell regain a momentum.

Figure 12:
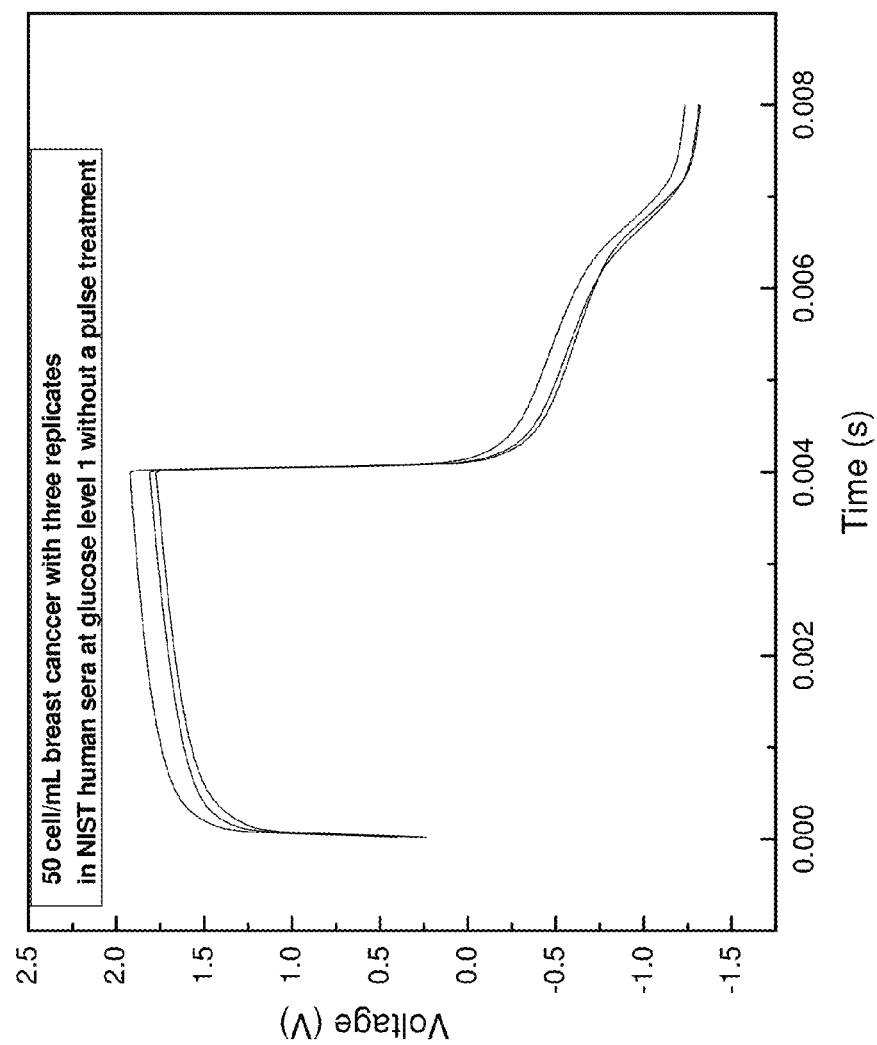
FIG. 12 illustrates three replicates of DSCPO curves of breast cancer 50 cell/mL in NIST standard human serum SRM 965A with certified blood glucose level 1 tested on Au/MCD/PEG/PVP sensor at room temperature at ±10 mA without any pre pulse treatments.
Figure 13:
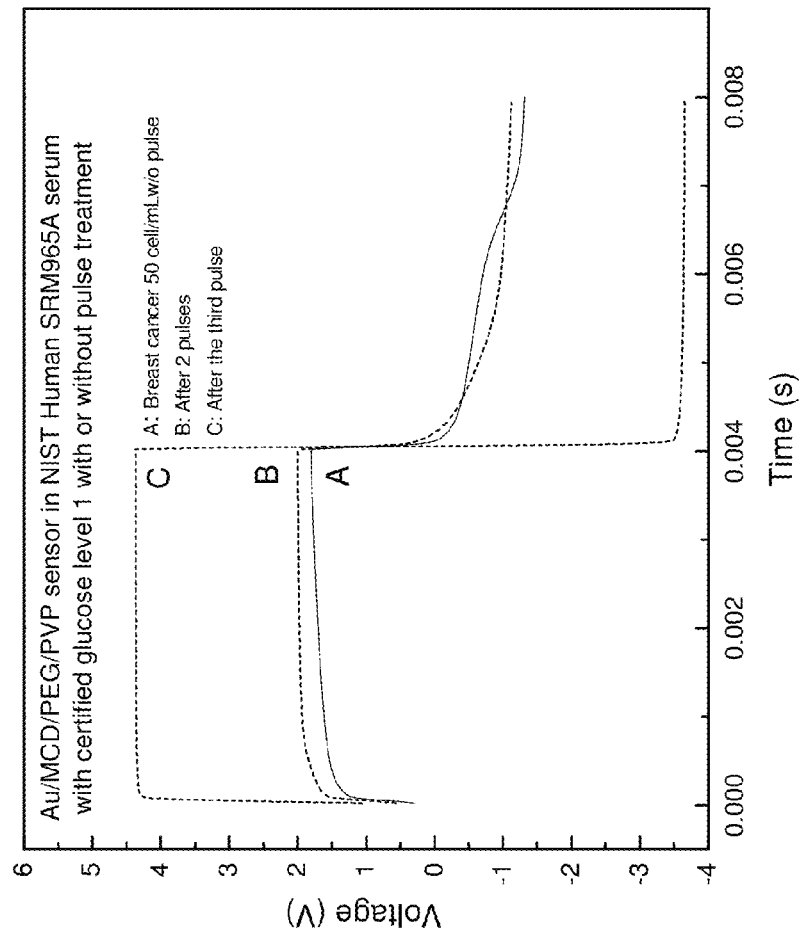
FIG. 13 illustrates the DSCPO curves of breast cancer 50 cell/mL in NIST standard human serum SRM 965A with certified blood glucose level 1 tested on Au/MCD/PEG/PVP sensor at room temperature at ±10 mA after pulse pre treatments: A: Breast cancer 50 cell/mL w/o pulse; B: After 2 pulses treatments; C: After the third pulse. Pulse treatments are shown in FIG. 11.

The ratio of the action/resting potential has changes from original 3.2±0.4 (cancer only) as shown in FIG. 12 to 2.37 and 1.19±0.01, for after second and third pulses, respectively as shown in FIG. 13 (B) and (C) compared with (A) without pulse. The method can restore the asymmetric curves of cancer cell "action/resting potential" to a normal more symmetric curve, and the ratio close to normal cell value of 0.8-0.9. The CV curves shown in FIG. 10 in D, the cancer finger print signal has completely gone, and reflected as the membrane potential ratio turned to in normal range.

Example 11

Applications

This contour map of multiple variable correlation method assesses the heat released by cancer cells and monitoring the cancer progress using the nanopore structured Biomimetic device opened a wide areas of applications in all cancer detection areas for visualization of the progress and easy to understand for patients and doctors with 1) higher sensitivity to 1 cell at early stage of cancer vs late stage of at least 10,000 cancer calls. can be seen on the image by the mammogram method; 2) Faster in ms to seconds vs 1 week the results can be known to patients; 3). Higher specificity of only recognize the single breast cancer cell against other type of cancer cell, like brain cancer cell has no interference with the results against the mammogram method, that can not distinguish brain cancer and breast cancer if both are in the brain; 4.) Portable and small size vs. a big machine for mammogram; 5) affordability. The new biomarker of ratio of the "Action/Resting" cell membrane potential provides a simplicity parameter for monitoring the cancer progress becomes the key component of the visual map will not only provide accurate, fast, sensitive testing results, but also portable and visual.

REFERENCES

1. B. Weiss, G. Ganepola, H. Freeman, Y. Hsu and M. Faupel, *Breast Disease,* 7(2), 91, (1994).
2. S. V. Sree, E. Ng, G. Kaw, R. Acharya-U, and B. Chong, *J. of Medical Systems,* 35(1). 79, 2011.
3. A. M. Hassan and M. Ei-Shenawee, Review of electyromagnetic techniques for beast cancer detection, *IEEE Transactions in magnetic, on line publisher,* 2011.
4. A. M. Hassan and M. Ei-Shenawee, The Diffusion-Drift Algorithm for Modeling the Biopotential Signals of Breast Tumors, #TTT-21, *Cancer Detection and Diagnostics Technologies for Global Health Symposium at National Cancer Institute,* Aug. 22-23, 2011.
5. D. Lewitus, R. J. Vogelstein, G. Zhen, Y-S Choi, J. Kohn, S. Hershberger, X-F Jia, *IEEE Transactions on neuronal systems and rehabilitation engineering* 19(2), 204, 2011.
6. L. G. Mitchell, N. A. Campbell, J. B. Reece and M. R. Taylor, *Biology,* 8$^{th}$ *edition,* 2007.
7. S. L. Bonifacio, H. C. Glass, D. M. Ferriero and S. Peloquin, *Nature Reviews Neruology* 7, 485, 2011.
8. E. Chen and H. L. Pardue, *Anal Chem.* 65, 2563-2567, 1993.
9. E. Chen, Novel Nanopore Structured Electrochemical Biosensor, U.S. Pat. No. 8,083,926, Dec. 27, 2011.
10. E. T. Chen, S-H Duh, C. Ngatchou, J. T. Thornton and P. T. Kissinger, *Nanotech* (3), 101-104, 2011.
11. E. T. Chen, J. Thornton, C. Ngatchou, S-H. Duh, P. T. Kissinger, study of the correlations between direct electron transfer rate constants and the effectiveness of cancer inhibitors using nanobiomimetic sensors, *NSTi*-Nanotech 3, 115-118, 2013.
12. E. Laviron, J. Electroanal Chem., 101, 19-28, 1979.

What is claimed is:

1. A direct single cancer cell detecting device comprising:
   an electrode comprising a substrate of gold;
   a self-assembling membrane comprising a polymer matrix comprised of an electrically conductive copolymer; wherein the copolymer is further comprised of: one or more first β-cyclodextrin molecules having at least one or more imidazolium groups; one or more polyethylene glycol polymers (PEG); and one or more poly(4-vinylpyridine) (PVP) polymers;
   wherein the self-assembling membrane has a nanobiomimetic surface structure comprising an array of nanopores, and the membrane also has active sites, and the nanopores are vertically oriented on the substrate, and wherein the device promotes an electron-relay network with imidazolium-ATP of single cancer cell-water-pyridine at its active sites of the membrane that mimic the electron-relaying between His 516 and N(5)-FAD of $GO_x$ in the presence of glucose.

2. The device according to claim 1, wherein receptors of imidazolium and pyridine form an electron-relay with receptors of breast cancer cells.

3. The device according to claim 2, wherein the membrane comprises cross-linked polymers.

4. The device according to claim 2, wherein the detected single cancer cell enhances the heterogonous electron transfer rate constant $k_s$ by 1.54-fold compared with that of a situation without the presence of the cancer cell in a cell culture media detected with the device where the direct electron transfer rate constant is 92/s.

5. The device according to claim 1, wherein the nanopores are on average 20 nm in diameter with a Root-Mean-Square (RMS) error 0.82 nm.

6. The device according to claim 1, wherein glucose concentration changes do not interfere with the electron-relay bio communication between receptors of the device membrane and the single cancer cell.

7. The device according to claim 1, wherein the sensor selectively detects triple-negative breast cancer cells at a single cancer cell concentration and rejects brain cancer cells.

8. The device according to claim 1, wherein the device is free from natural enzymes.

9. The device according to claim 1, wherein the device is free from antibody.

10. The device according to claim 1, wherein the device is free from mediator and labeling.

11. The device according to claim 1, wherein the device is free from electrolyte channeling interference.

12. The device according to claim 1, wherein the device is not able to form an electro-relay biocommunication with brain cancer cell that is a single glioblastoma brain cancer cell.

13. A method of using the device according to claim 1, further including the use for direct measuring cancer biocommunication voltage change comprising:
   a) obtaining a sample immersed in a media which can be detected;
   b) contacting the sample with the device, the device has the β-cyclodextrin molecules; in the form of a nanopore array and chemically modified to be bioelectro-communicationally active in the network affixed to said electrode;

c) setting up an appropriate fixed pulse current and applying the current onto the device;

d) setting up an appropriate pulse stepping time in order to measure voltage;

e) and measuring the cell voltage in the media.

14. The device according to claim 1, wherein the device is portable.

15. A method of measuring the concentration of living cancer cells in a sample immersed in cell culture media, the method comprises: obtaining a sample in cell culture media which can be detected; contacts the sample with a sensor, the sensor comprises an electrode having a cyclodextrin in the form of a nanopore array and is chemically modified to be bioelectro-communicationally active in a net work affixed to said electrode; and measuring the concentration of the living cancer cells in the cell culture media and without pretreatment, except dilutions.

16. The method according to claim 15, wherein the sample is comprised of a bodily fluid.

* * * * *